(12) United States Patent
Katsuyama

(10) Patent No.: US 9,291,601 B2
(45) Date of Patent: Mar. 22, 2016

(54) AMBIENT SOUND VELOCITY OBTAINING METHOD AND APPARATUS

(75) Inventor: Kimito Katsuyama, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 478 days.

(21) Appl. No.: 13/638,501

(22) PCT Filed: Mar. 31, 2011

(86) PCT No.: PCT/JP2011/001949
§ 371 (c)(1),
(2), (4) Date: Sep. 28, 2012

(87) PCT Pub. No.: WO2011/122044
PCT Pub. Date: Oct. 6, 2011

(65) Prior Publication Data
US 2013/0030297 A1    Jan. 31, 2013

(30) Foreign Application Priority Data
Mar. 31, 2010    (JP) .................. 2010-080596

(51) Int. Cl.
*G01N 29/07* (2006.01)
*A61B 8/08* (2006.01)
*G01S 7/52* (2006.01)

(52) U.S. Cl.
CPC .............. *G01N 29/07* (2013.01); *A61B 8/0858* (2013.01); *G01S 7/52049* (2013.01)

(58) Field of Classification Search
CPC .... G01S 15/8906; A61B 6/52; A61B 5/1128; A61B 8/00; A61B 8/52; G06T 7/0012
See application file for complete search history.

(56) References Cited

U.S. PATENT DOCUMENTS

| 6,305,225 B1 | 10/2001 | Bae et al. |
| 2008/0168839 A1* | 7/2008 | Katsuyama .................. 73/602 |

(Continued)

FOREIGN PATENT DOCUMENTS

| JP | 08-308832 A | 11/1996 |
| JP | 2000-166925 A | 6/2000 |

(Continued)

OTHER PUBLICATIONS

Chinese Office Action dated May 6, 2014 issued in Chinese patent application No. 201180015136.4.

(Continued)

*Primary Examiner* — Tse Chen
*Assistant Examiner* — Nate S Sunwoo
(74) *Attorney, Agent, or Firm* — Sughrue Mion, PLLC

(57) ABSTRACT

To obtain ambient sound velocity of a subject with high accuracy in a ultrasonic diagnosis apparatus. In an ambient sound velocity obtaining method that transmits ultrasonic waves from an ultrasonic probe, receives reflected waves reflected by a subject to obtain received signals, performs a receive focusing process on the received signals using receive delay times based on a plurality of sound velocity settings to obtain in-phase sum signals with respect to each sound velocity setting, and obtains an ambient sound velocity of the subject based on the in-phase sum signals with respect to each sound velocity setting, the in-phase sum signals with respect to each sound velocity setting is separated into an in-phase sum signal corresponding to a boundary portion in the subject and an in-phase sum signal corresponding to portions other than the boundary portion, an index is obtained based on at least either one of the in-phase sum signals, and the ambient sound velocity is obtained based on the index.

10 Claims, 7 Drawing Sheets

(56) References Cited

U.S. PATENT DOCUMENTS

2009/0099451 A1    4/2009    Nakaya et al.
2010/0076312 A1*    3/2010    Katsuyama .................. 600/443

FOREIGN PATENT DOCUMENTS

| | | |
|---|---|---|
| JP | 2009-089940 A | 4/2009 |
| JP | 2010-017530 A | 1/2010 |
| JP | 2010-119481 A | 6/2010 |
| WO | 01/26555 A1 | 4/2001 |

OTHER PUBLICATIONS

Japanese Office Action dated Nov. 5, 2013 issued in Japanese Patent Application No. 2010-080596.

* cited by examiner

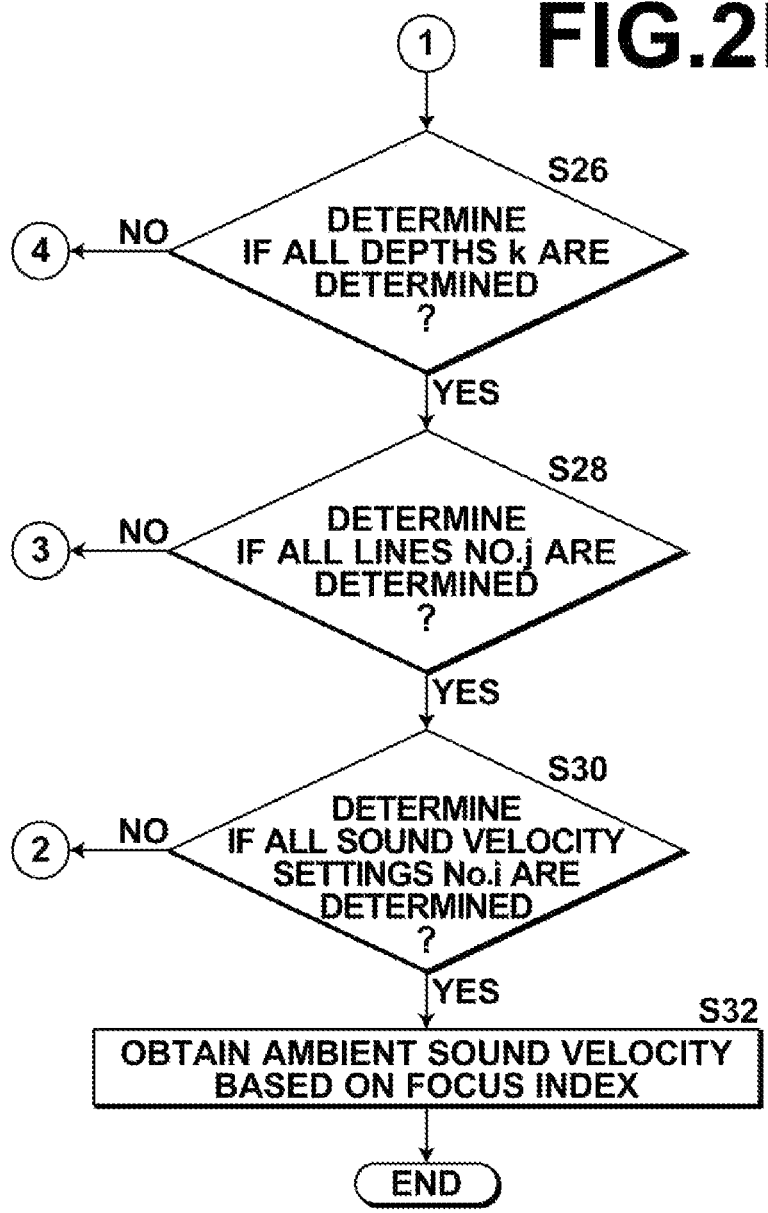

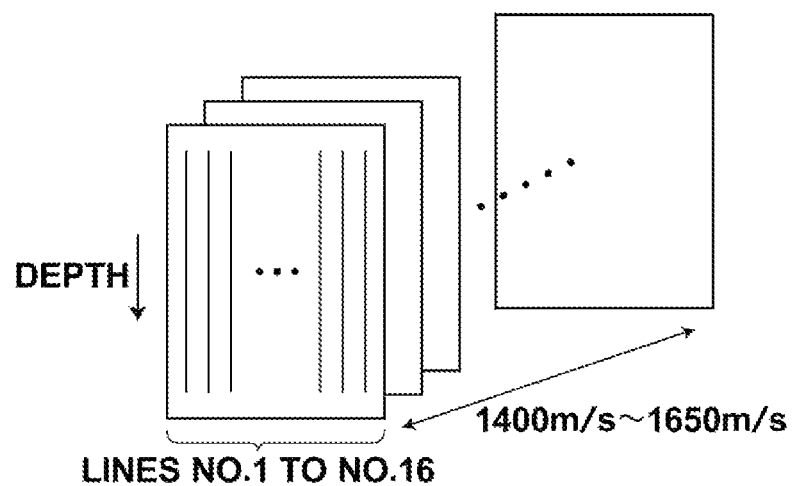
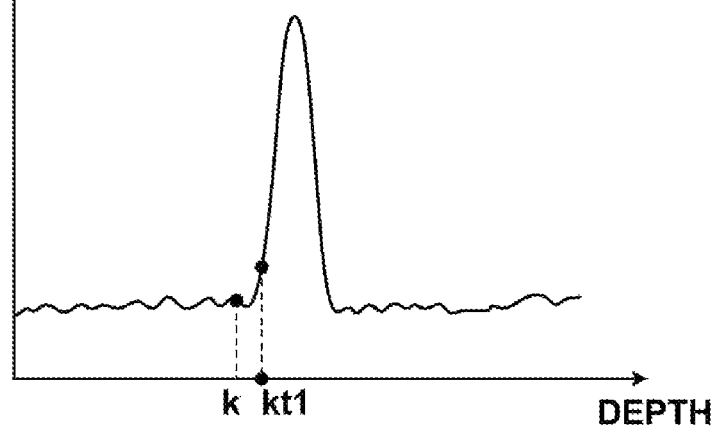

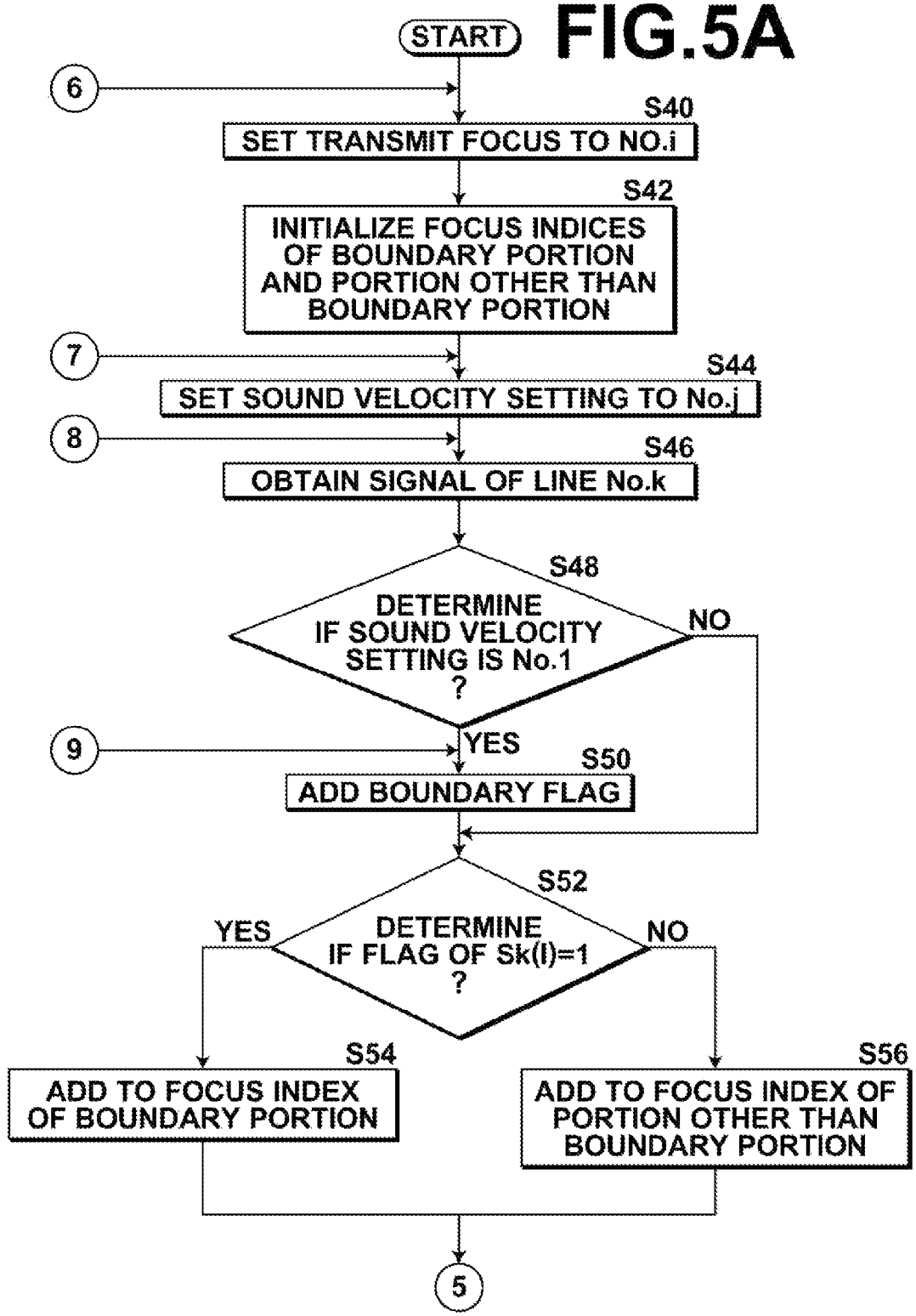

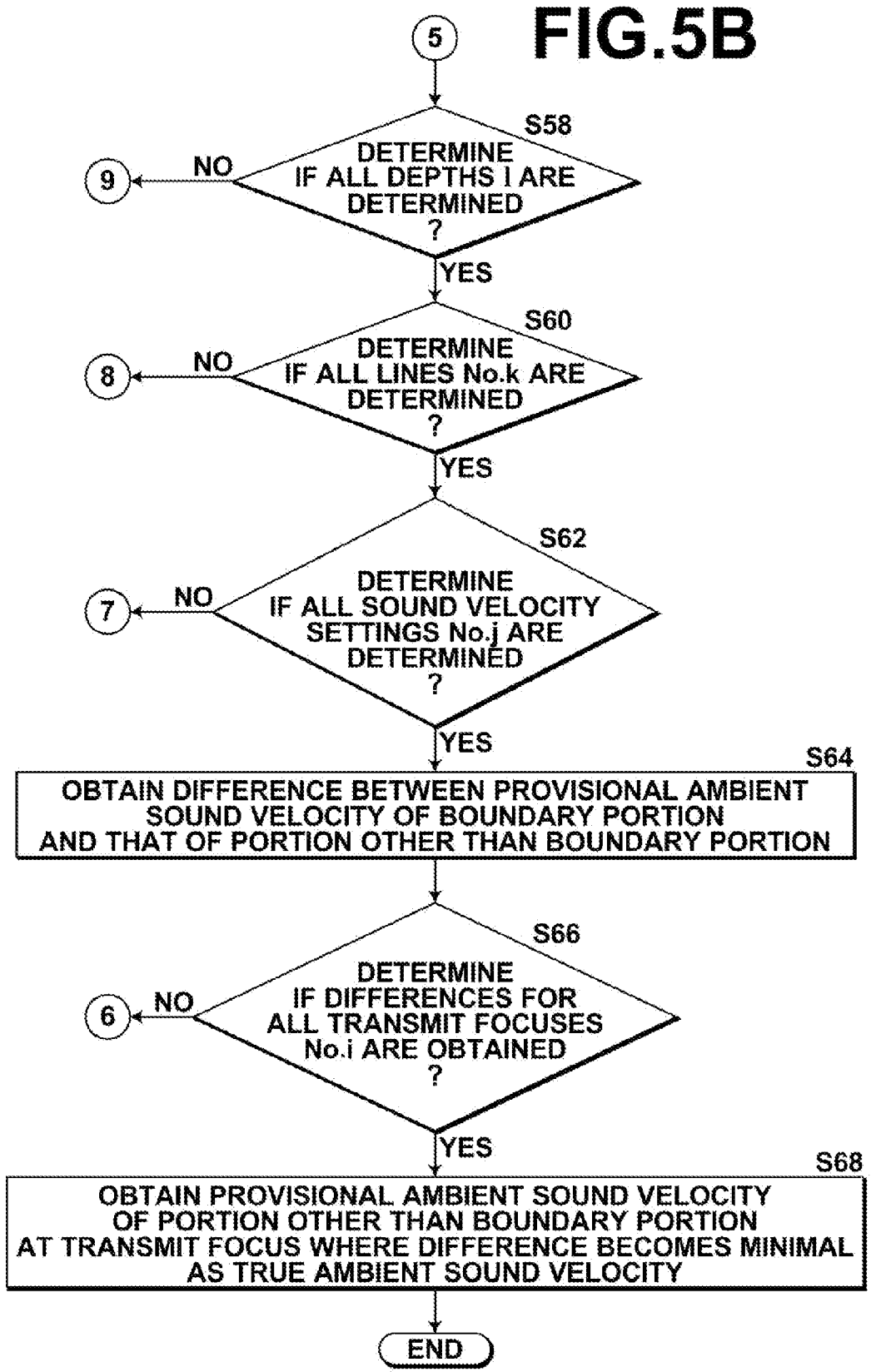

AMBIENT SOUND VELOCITY OBTAINING METHOD AND APPARATUS

CROSS REFERENCE TO RELATED APPLICATIONS

This application is a National Stage of International Application No. PCT/JP2011/001949 filed Mar. 31, 2011, claiming priority based on Japan Patent Application No. 2010-080596, filed Mar. 31, 2010, the contents of all of which are incorporated herein by reference in their entirety.

TECHNICAL FIELD

The present invention relates to a method and apparatus for obtaining an ambient sound velocity of a subject used in an ultrasonic diagnostic apparatus.

BACKGROUND ART

Ultrasonic diagnostic apparatuses for obtaining a tomographic image of a subject using ultrasonic waves for medical diagnosis have been proposed. In such an ultrasonic diagnostic apparatus, when transmitting ultrasonic waves from an ultrasonic probe, so-called transmit focusing in which a transmit delay time is set to each ultrasonic wave transmitted from each element of the ultrasonic probe is performed and when obtaining receive signals, so-called receive focusing in which a receive time delay is set to each signal received by each element is performed in order to improve azimuth resolution.

When such transmit focusing and receive focusing are carried out, a representative sound velocity of the diagnostic target region is assumed and transmit delay times and receive delay times are set based on the assumed sound velocity.

But, the ambient sound velocity of a subject is not constant and differs from tissue to tissue, and if the assumed sound velocity differs from the ambient sound velocity, a problem of image quality degradation may arise.

One reason for image quality degradation is that the transmit delay times of transmit focusing or receive delay times of receive focusing differ from the transmit delay times for properly forming a transmit focal point on a target or receiving times of ultrasonic waves reflected from the target and received by the respective elements of the ultrasonic probe.

The term "ambient sound velocity" as used herein refers to a sound velocity determined based on the distance from a predetermined target to each element and the receiving time of each element when the ultrasonic wave is transmitted to the target.

Attempts have been made to prevent the image quality degradation by matching the assumed sound velocity with the ambient sound velocity.

For example, Japanese Unexamined Patent Publication No. 2009-089940 proposes a method in which receive focusing is performed on echo signals received by transmitting ultrasonic waves using receive delay times based on a plurality of sound velocity settings to generate a plurality of ultrasonic images of different sound velocity settings, then contrasts of the plurality of ultrasonic images are compared, and an ultrasonic image having a maximum contrast is displayed.

When capturing an ultrasonic image, transmit focusing is performed on the ultrasonic waves so as to be focused on a predetermined focus position before being transmitted. For example, in the case where the transmit focus position is at a depth of 20 mm and a boundary portion which is parallel to the probe surface, such as a surface of an internal organ, is present at a position around 22 mm, which is deeper than the transmit focus position, as illustrated in FIG. 6A, the time at which a reflection wave is received by the element located directly under the transmit focus is after a round-trip propagation time of the ultrasonic wave to and from the boundary, as the ultrasonic wave is specular reflected at the boundary portion. On the other hand, a time delay of an element around it corresponds to the time delay of a point reflection at a position deeper than the boundary, that is, an ambient sound velocity at the boundary portion seems faster than that at a portion other than the boundary portion. In the mean time, for example, in the case where the transmit focus position is deeper (24 mm) than a boundary portion, which is parallel to the probe surface, located about 22 mm deep, as illustrated in FIG. 6B, the ultrasonic wave is specular reflected at the boundary portion also in this case, so that the time at which a reflection wave is received by the element located directly under the transmit focus is after a round-trip propagation time of the ultrasonic wave to and from the boundary. On the other hand, a time delay of an element around it corresponds to the time delay of a point reflection at a position shallower than the boundary, that is, an ambient sound velocity at the boundary portion seems slower than that at a portion other than the boundary portion.

Further, if the boundary surface is not parallel to the probe surface or curved, more complicated reflection behaviors are seen, and the ambient sound velocity at the boundary portion differs from that of a portion other than the boundary portion after all.

Therefore, receive focusing performed by setting sound velocity settings without making a distinction between the boundary portion and a portion other than the boundary portion, as in the method described in Japanese Unexamined Patent Publication No. 2009-089940, may result in that appropriate contrasts may not be obtained due to noise caused by the contrast at the boundary portion, so that an ambient sound velocity of a subject may not be obtained.

The present invention is developed in view of the circumstances described above, and it is an object of the present invention to provide an ambient sound velocity obtaining method and apparatus capable of obtaining an ambient sound velocity of a subject with high accuracy.

DISCLOSURE OF INVENTION

An ambient sound velocity obtaining method of the present invention is a method in which an ultrasonic wave is transmitted into a subject from an ultrasonic probe, a reflection wave reflected from the subject by the transmission of the ultrasonic wave is received by the ultrasonic probe to obtain a receive signal, receive focusing is performed on the receive signal using receive delay times based on a plurality of sound velocity settings to obtain in-phase sum signals with respect to each sound velocity setting, and an ambient sound velocity of the subject is obtained based on the obtained in-phase sum signals with respect to each sound velocity setting, wherein the method includes the steps of:

a separation step for separating the in-phase sum signals with respect to each sound velocity setting into an in-phase sum signal corresponding to a boundary portion in the subject and an in-phase sum signal corresponding to a portion other than the boundary portion;

an index obtaining step for obtaining an index based on at least either one of the in-phase sum signal corresponding to the boundary portion and the in-phase sum signal corresponding to the portion other than the boundary portion; and an ambient sound velocity obtaining step for obtaining the ambient sound velocity based on the obtained index.

In the ambient sound velocity obtaining method described above, the index obtaining step may be a step in which an index based on the in-phase sum signal corresponding to the boundary portion and an index based on the in-phase sum signal corresponding to the portion other than the boundary portion are obtained, and the ambient sound velocity obtaining step may be a step in which the ambient sound velocity is obtained based on the obtained index based on the in-phase sum signal corresponding to the boundary portion and the index based on the in-phase sum signal corresponding to the portion other than the boundary portion.

Further, the ultrasonic wave focused on a plurality of transmit focus positions may be transmitted with respect to each transmit focus position, the ambient sound velocity obtaining step may be a step in which an index of the boundary portion and an index of the portion other than the boundary portion are obtained with respect to each transmit focus position, the ambient sound velocity obtaining step may includes the steps of obtaining a difference between a provisional ambient sound velocity obtained base on the index of the boundary portion and a provisional ambient sound velocity obtained based on the index of the portion other than the boundary portion with respect to each focus position and obtaining a provisional ambient sound velocity obtained based on the index of the boundary portion or the index of the portion other than the boundary portion corresponding to a transmit focus position where the difference obtained becomes minimal as the ambient sound velocity of the subject.

Still further, the boundary portion may be determined based on a ratio between in-phase sum signals disposed in a depth direction of the subject, or a first or second derivative value using the logarithm of the in-phase sum signals.

An ambient sound velocity obtaining apparatus of the present invention is an apparatus which includes a transmission control section for transmitting an ultrasonic wave into a subject from an ultrasonic probe, a receiving control section for receiving a reflection wave reflected from the subject by the transmission of the ultrasonic wave by the ultrasonic probe to obtain a receive signal and performing receive focusing on the obtained receive signal using receive delay times based on a plurality of sound velocity settings to obtain in-phase sum signals with respect to each sound velocity setting, and an ambient sound velocity obtaining section for obtaining an ambient sound velocity of the subject based on the in-phase sum signals obtained by the receiving control section with respect to each sound velocity setting, wherein the ambient sound velocity obtaining section is a section that separates the in-phase sum signals with respect to each sound velocity setting into an in-phase sum signal corresponding to a boundary portion in the subject and an in-phase sum signal corresponding to a portion other than the boundary portion, obtains an index based on at least either one of the in-phase sum signal corresponding to the boundary portion and the in-phase sum signal corresponding to the portion other than the boundary portion, and obtains the ambient sound velocity based on the obtained index.

In the ambient sound velocity obtaining apparatus of the present invention described above, the ambient sound velocity obtaining section may be a section that obtains an index based on the in-phase sum signal corresponding to the boundary portion and an index based on the in-phase sum signal corresponding to the portion other than the boundary portion and obtains an ambient sound velocity based on the obtained index based on the in-phase sum signal corresponding to the boundary portion and the index based on the in-phase sum signal corresponding to the portion other than the boundary portion.

Further, the transmission control section may be a section that transmits the ultrasonic wave focused on a plurality of transmit focus positions with respect to each transmit focus position, and the ambient sound velocity obtaining section may be a section that obtains an index of the boundary portion and an index of the portion other than the boundary portion with respect to each transmit focus position, obtains a difference between a provisional ambient sound velocity obtained base on the index of the boundary portion and a provisional ambient sound velocity obtained based on the index of the portion other than the boundary portion with respect to each focus position, and obtains a provisional ambient sound velocity obtained based on the index of the boundary portion or the index of the portion other than the boundary portion corresponding to a transmit focus position where the difference obtained becomes minimal as the ambient sound velocity of the subject.

Still further, the ambient sound velocity obtaining section may be a section that determines the boundary portion based on a ratio between in-phase sum signals disposed in a depth direction of the subject, or a first or second derivative value using the logarithm of the in-phase sum signals.

According to the ambient sound velocity obtaining method and apparatus of the present invention, in an ambient sound velocity obtaining method in which receive focusing is performed on a receive signal obtained by the ultrasonic probe using receive delay times based on a plurality of sound velocity settings to obtain in-phase sum signals with respect to each sound velocity setting, and an ambient sound velocity of the subject is obtained based on the obtained in-phase sum signals with respect to each sound velocity setting, the in-phase sum signals with respect to each sound velocity setting are separated into an in-phase sum signal corresponding to a boundary portion in the subject and an in-phase sum signal corresponding to a portion other than the boundary portion, an index based on at least either one of the in-phase sum signal corresponding to the boundary portion and the in-phase sum signal corresponding to the portion other than the boundary portion is obtained, and the ambient sound velocity is obtained based on the obtained index. This allows a high accurate ambient sound velocity to be obtained without being influenced by a reflection at a boundary portion described above.

In the case where the transmit focus position is set to the boundary portion described above, the ambient sound velocity of the boundary portion coincides with that of a portion other than the boundary portion.

In the ambient sound velocity obtaining method and apparatus of the present invention, if an arrangement is adopted in which the ultrasonic wave focused on a plurality of transmit focus positions is transmitted with respect to each transmit focus position, an index of the boundary portion and an index of the portion other than the boundary portion are obtained with respect to each transmit focus position, a difference between a provisional ambient sound velocity obtained base on the index of the boundary portion and a provisional ambient sound velocity obtained based on the index of the portion other than the boundary portion is obtained with respect to each transmit focus position, and a provisional ambient sound velocity obtained based on the index of the boundary portion or the index of the portion other than the boundary portion corresponding to a transmit focus position where the difference obtained becomes minimal is obtained as the ambient sound velocity of the subject, the ambient sound velocity when the transmit focus position is set to the boundary section may be obtained easily and a high accurate ambient sound velocity may be obtained.

BRIEF DESCRIPTION OF DRAWINGS

FIG. 2B is a flowchart illustrating a first embodiment of the ambient sound velocity obtaining method of the present invention.

FIG. 3 illustrates an in-phase sum signal obtained with respect to each sound velocity setting.

FIG. 4 illustrates how to set a boundary graph.

FIG. 5A is a flowchart illustrating a second embodiment of the ambient sound velocity obtaining method of the present invention.

FIG. 5B is a flowchart illustrating a second embodiment of the ambient sound velocity obtaining method of the present invention.

BEST MODE FOR CARRYING OUT THE INVENTION

Figure 1:
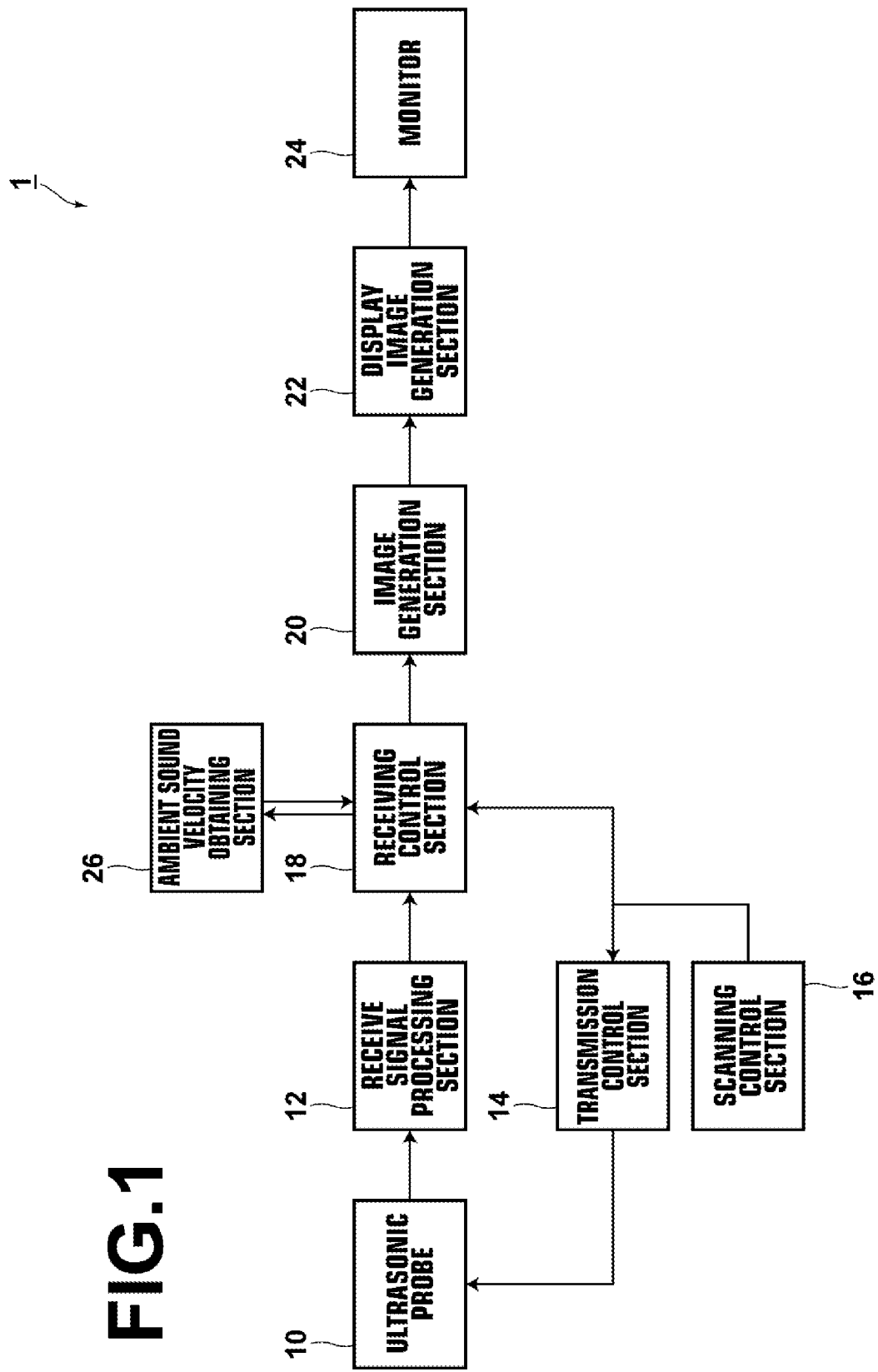
FIG. 1 is a block diagram of an ultrasonic diagnostic apparatus utilizing an embodiment of the ambient sound velocity obtaining apparatus of the present invention, illustrating a schematic configuration thereof.

Hereinafter, an ultrasonic diagnostic apparatus utilizing an embodiment of the ambient sound velocity obtaining apparatus of the present invention will be described in detail with reference to the accompanying drawings. FIG. 1 is a block diagram of the ultrasonic diagnostic apparatus of the present embodiment, illustrating a schematic configuration thereof. The ultrasonic diagnostic apparatus 1 of the present embodiment includes an ultrasonic probe 10, a receive signal processing section 12, a transmission control section 14, a scanning control section 16, a receiving control section 18, an image generation section 20, a display image generation section 22, a monitor 24, and an ambient sound velocity obtaining section 26.

The ultrasonic probe 10 is a probe for transmitting an ultrasonic wave toward a diagnostic target region in a subject body and receiving an ultrasonic wave reflected from inside of the body. The ultrasonic probe 10 of the present embodiment includes a plurality of ultrasonic transducers forming a one-dimensional ultrasonic transducer array, and each ultrasonic transducer is a vibrator formed, for example, of a piezoelectric element, such as a PZT or the like, with an electrode formed on each side. The electrodes are connected to the receive signal processing section 12 and transmission control section 14 by signal wires. A voltage according to a drive pulse voltage signal outputted from the transmission control section 14 is applied between the electrodes, and the vibrator generates an ultrasonic wave according to the applied voltage. Further, the vibrator generates an electrical signal upon receipt of a reflected ultrasonic wave and outputs the electrical signal to the receive signal processing section 12 as the receive signal.

The transmission control section 14 causes the ultrasonic wave that will converge at a predetermined focus to be outputted from the ultrasonic probe 10 by outputting a drive pulse voltage signal to each ultrasonic transducer of the ultrasonic probe 10 based on a transmit delay time outputted from the scanning control section 16 and causing the vibrator of each ultrasonic transducer to transmit an ultrasonic wave according to the transmit delay time.

The receive signal processing section 12 includes a plurality of amplifiers and A/D converters, each pair of the amplifier and A/D converter corresponding to each transducer of the ultrasonic probe 10. The receive signal outputted from each ultrasonic transducer is amplified by the amplifier, then the analog receive signal outputted from the amplifier is converted to a digital receive signal by the A/D converter, and the digital receive signal is outputted to the receiving control section 18.

The receiving control section 18 outputs an in-phase sum signal of narrowly focused ultrasonic echo by performing receive focusing on a plurality of receive signals outputted from a plurality of ultrasonic transducers of the ultrasonic probe 10 based on predetermined receive delay times outputted from the scanning control section 16.

The scanning control section 16 controls transmit focusing and receive focusing by outputting transmit delay times and receive delay times to the transmission control section 14 and receiving control section 18 respectively.

The image generation section 20 generates an ultrasonic image signal representing tomographic image information of a tissue in a subject based on the in-phase sum signal outputted from the receiving control section 18.

The display image generation section 22 generates a display control signal based on the ultrasonic image signal outputted from the image generation unit 20 and outputs the generated display control signal to the monitor 24.

The monitor 24 displays an ultrasonic image of a subject based on the inputted display control signal or an ambient sound velocity obtained by the ambient sound velocity obtaining section 26 as a numerical value.

The ambient sound velocity obtaining section 26 obtains, based on an in-phase sum signal other than that corresponding to a boundary portion in a subject, a focus index of a portion other than the boundary portion and obtains an ambient sound velocity of the subject based on the obtained focus index of the portion other than the boundary portion. The method for obtaining the ambient sound velocity will be described in detail later.

An operation of the ultrasonic diagnostic apparatus of the present embodiment will now be described. The ultrasonic diagnostic apparatus of the present embodiment is characterized by the method of obtaining an ambient sound velocity of a subject. But, an operation for displaying an ultrasonic image in a subject will be described first.

First, a drive pulse voltage signal is outputted from the transmission control section 14 to each ultrasonic transducer of the ultrasonic probe 10 based on a control signal according to a transmit delay time outputted from the scanning control section 16. Here, a different transmit delay time is set to each drive pulse voltage signal such that the ultrasonic wave transmitted from each ultrasonic transducer converges at a preset focal point. The transmit delay times are values calculated in advance based on an assumed sound velocity setting set by assuming ambient sound velocity in the subject.

Then, the vibrator of each ultrasonic transducer of the ultrasonic probe 10 vibrates mechanically by receiving the drive pulse voltage signal described above, whereby an ultrasonic wave is generated and transmitted to the subject.

The ultrasonic wave transmitted from each ultrasonic transducer propagates the subject and is reflected successively at discontinuity surfaces of acoustic impedance and the echo of the reflection is detected by each ultrasonic transducer and the vibrator vibrates. This vibration causes a weak electrical signal to be generated from the vibrator of each ultrasonic transducer and the electrical signal is outputted to the receive signal processing section 12 as the receive signal.

In the receive signal processing section 12, the receive signal outputted from each ultrasonic transducer is amplified by the amplifier and the amplified signal is converted to a digital receive signal by the A/D converter and the digital receive signal is outputted to receiving control section 18.

In the receiving control section 18, receive focusing is performed on a plurality of receive signal outputted from a plurality of ultrasonic transducers based on predetermined receive delay times outputted from the scanning control section 16 and an in-phase sum signal is generated. The receive delay times outputted from the scanning control section 16 are values calculated based on an assumed sound velocity setting set by assuming ambient sound velocity in the subject in advance such that the in-phase sum signal corresponds to the signal presented at a predetermined focal point in the subject.

Then, by controlling the receive delay times outputted from the scanning control section 16, an in-phase sum signal of each focal point within the imaging range in the subject is obtained by the receiving control section 18 and the in-phase sum signals are sequentially outputted to the image generation section 20.

The image generation section 20 stores the inputted in-phase sum signals in series, then generates an ultrasonic image signal representing tomographic image information of the subject, and outputs the ultrasonic image signal to the display image generation section 22.

In the display image generation section 22, a display control signal is generated based on the inputted ultrasonic image signal and the display control signal is outputted to the monitor 24. The monitor 24 displays an ultrasonic image of the subject based on the inputted display control signal.

Thereafter, the ultrasonic wave transmission from each ultrasonic transducer of the ultrasonic probe 10 is carried out according to a predetermined frame rate, and the aforementioned steps are repeated to display an ultrasonic image at the predetermined frame rate in succession.

So far the operation of the ultrasonic diagnostic apparatus of the present embodiment for displaying an ultrasonic image has been described.

Figure 2A:
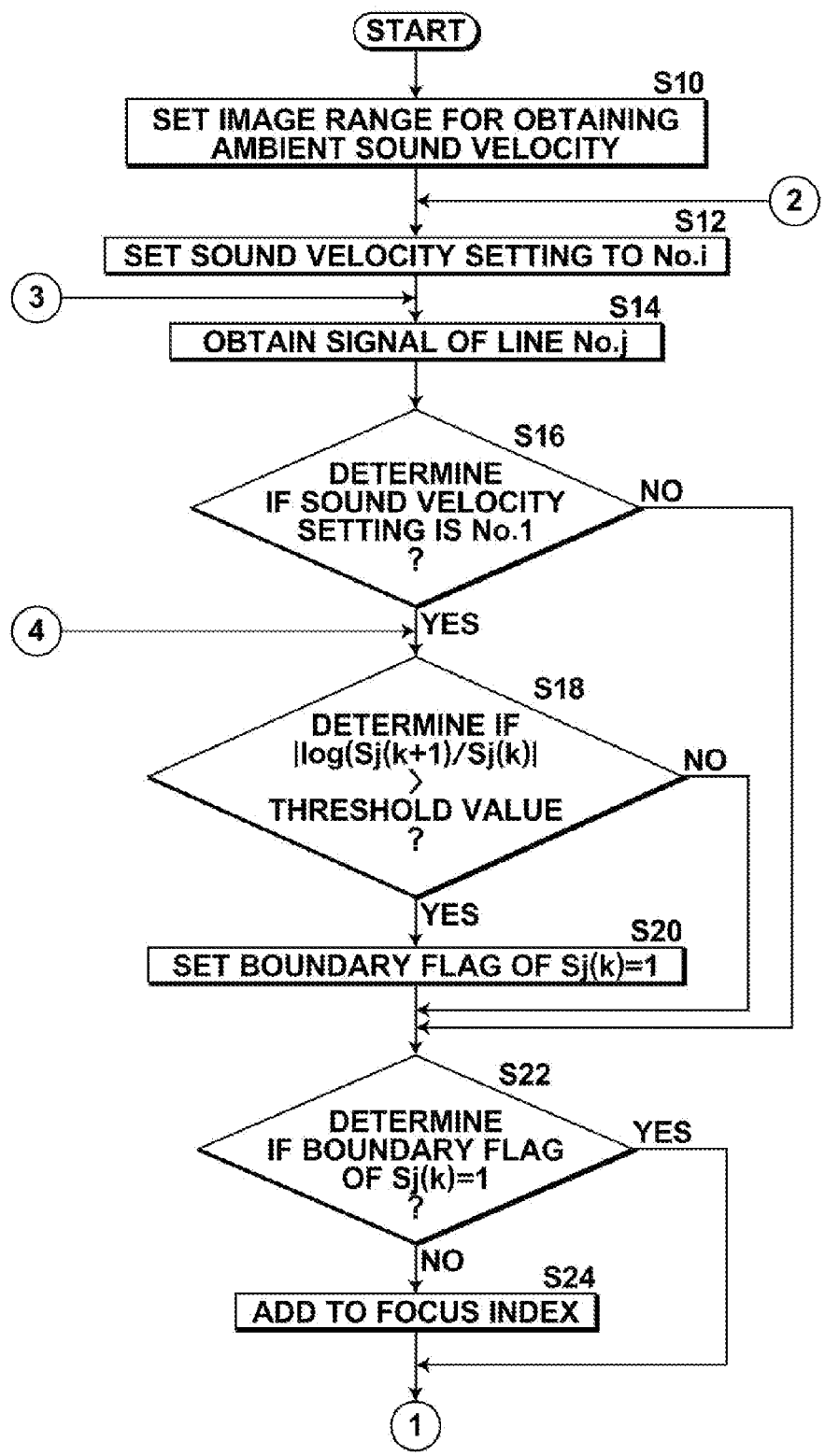
FIG. 2A is a flowchart illustrating a first embodiment of the ambient sound velocity obtaining method of the present invention.
Figure 6A:
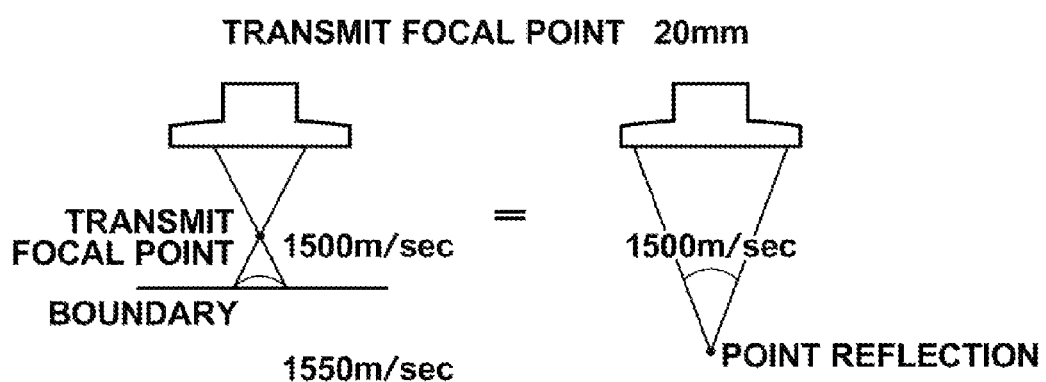
FIG. 6A illustrates influence of reflection in the case where a boundary portion is present in a subject at a position deeper than a transmit focus position.
Figure 6B:
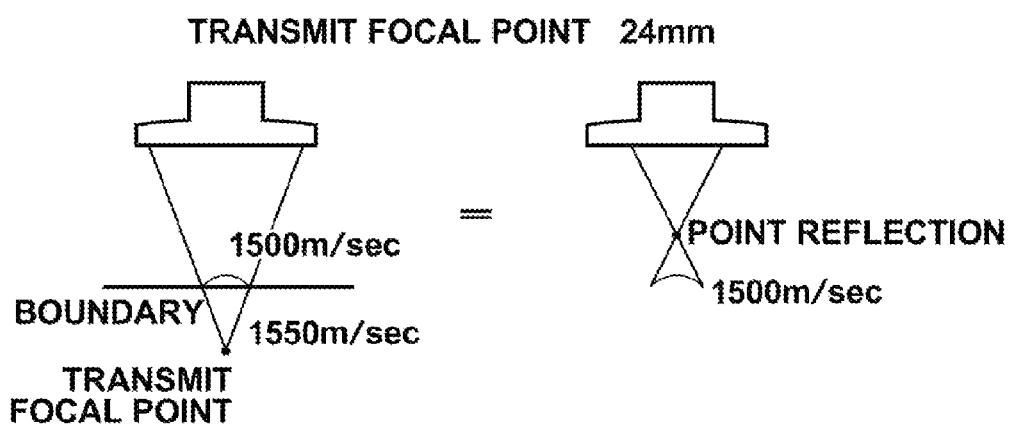
FIG. 6B illustrates influence of reflection in the case where a transmit focus is at a position deeper than a boundary portion in a subject.

Next, a method for obtaining an ambient sound velocity of a subject by the ultrasonic diagnostic apparatus 1 described above will be described. The ambient sound velocity obtaining method is embodied in two ways, first and second embodiments, and the first embodiment will be described now with reference to the flowchart shown in FIGS. 2A, 2B.

First, during an image capturing operation for capturing an ultrasonic image like that described above, a range of the ultrasonic image for obtaining the ambient sound velocity is specified (S10). The range may be set prior to obtaining the ultrasonic image or may be specified by the operator using a predetermined input device during the image capturing operation. In the case where it is specified by the operator, an arrangement may be adopted in which an arbitrary range is specified by the operator in an ultrasonic image displayed on the monitor 24. In the present embodiment, the size of the range is 16 lines with a depth of 3 mm to 4 mm, as described later.

Then, based on a preset transmit focus position, drive pulse voltage signals are outputted from the transmission control section 14 and an ultrasonic wave is transmitted from each ultrasonic transducer of the ultrasonic probe 10. Note that the transmit delay times here are values calculated in advance based on an assumed sound velocity setting set by assuming an ambient sound velocity in the subject.

Then an echo due to reflection of the ultrasonic wave transmitted from each ultrasonic transducer is detected by each ultrasonic transducer, and the receive signal is outputted to the receive signal processing section 12 where the signal is subjected to amplification and A/D conversion before being outputted to the receiving control section 18.

The receiving control section 18 performs receive focusing on the receive signals using receive delay times calculated based on a preset sound velocity setting No.1 and calculates an in-phase sum signal for line No.1 and outputs the signal to the ambient sound velocity obtaining section 26 (S12).

In the present embodiment, as sound velocity setting No.1 for calculating receive delay times, No.1 to No.251 are preset in the scanning control section 16. More specifically, the sound velocity settings No.1 to No.251 are from 1400 m/s to 1650 m/s and each sound velocity setting is set at an increment of 1 m/s. The scanning control section 16 calculates receive delay times based on the sound velocity settings and outputs the calculated receive delay times to the receiving control section 18.

Further, line No.j represents in-phase sum signals of one column extending in a depth direction of the subject and is a line set within the range for obtaining the ambient sound velocity. In the present embodiment, 16 columns of lines No.1 to No.16 are used.

Then, if the sound velocity setting used for the receive focusing is No.1 (S16), a determination is made as to whether or not each in-phase sum signal S1($k$) of line No.1 is that belonging to a boundary portion of the subject (S18). Note that k represents a depth in the range set for obtaining the ambient sound velocity of the subject.

More specifically, as illustrated in FIG. 4, a logarithm is taken for the ratio between adjacent in-phase sum signals S1($k$) and S1($k$+1) and a determination is made as to whether or not the absolute value of the logarithm is greater than a predetermined threshold value. If the absolute value is greater than the predetermined threshold value, the in-phase sum signal S1($k$) is determined to belong to the boundary portion, and a boundary flag is set (=1) to the depth k of the in-phase sum signal S1($k$) (S20).

In the present embodiment, a logarithm of the ratio between adjacent in-phase sum signals is used for the determination, as described above, but the determination may also be made, for example, by calculating and using a first or second derivative value of a logarithm of in-phase sum signals disposed in the depth direction.

The determination may also be made by calculating and using a difference in absolute value between adjacent in-phase sum signals. The absolute value of an in-phase sum signal is likely to be influenced by the position of transmit focus, scattering, attenuation, and the like and there may be a case in which a correct determination cannot be made if the difference in absolute value between adjacent in-phase sum signals. Therefore, the ratio between adjacent in-phase sum signals, or a first or second derivative value of the logarithm of in-phase sum signals described above is preferably used.

Then, an in-phase sum signal at depth k to which the boundary flag=1 is not set is added to the focus index for obtaining the ambient sound velocity of the subject (S22, S24). On the other hand, an in-phase sum signal at depth k to which the boundary flag=1 is set is not added to the focus index for obtaining the ambient sound velocity of the subject.

Each in-phase sum signals S1($k$) of line No.1 is determined if it belongs to the boundary portion in the subject in the manner described above and, if it does not belong to the boundary portion, it is added to the focus index (S26).

Thereafter, the receive focusing target line is sequentially changed to lines No.2 to No.16 by the receiving control section 18 and the steps from S14 to S26 are repeated with respect to in-phase sum signals of each line, and only in-phase signals not belonging to the boundary portion of in-phase sum signals Sj(k) of each line are added to the focus index in series (S28).

With respect to each of the in-phase sum signals of lines No.1 to No.16 subjected to the receive focusing using receive delay times based on the sound velocity setting No.1, a determination is made as to whether or not it belongs to the boundary portion and the flag is set in the manner described above. Then, only in-phase sum signals not belonging to the boundary portion are added up and a first focus index is calculated.

Next, the receiving control section 18 changes the receive delay times to those calculated based on the sound velocity setting No.2 (S30, S12), calculates in-phase sum signals of line No.1 by performing receive focusing on receive signals using the changed receive delay times, and outputs the calculated in-phase sum signals to the ambient sound velocity obtaining section 26 (S14).

Next, if the sound velocity setting is No.2, that is, not the one set first (S16), the boundary flags are not newly set.

Then, using the same boundary flag as that set to coordinate value of the line No.1 when the sound velocity setting was No.1, a determination is made as to whether or not each in-phase sum signal belongs to the boundary portion (S22). That is, the value of the boundary flag set to the coordinate value of each line No.j when sound velocity setting is No.1 is the same as that set to the coordinate value of each line No.j when the sound velocity setting is No.2.

Then, in the step S22, an in-phase sum signal of coordinate values to which the boundary flag=1 is not set, that is an in-phase sum signal not belonging to the boundary portion is added up as a second focus index for obtaining the ambient sound velocity of the subject (S22, S24).

Each of all the in-phase sum signals S1(k) of the line No.1 is determined whether or not it belongs to a boundary portion of the subject in the manner described above, and each in-phase signal not belonging to the boundary portion is added up to the second focus index (S26).

Thereafter, the receive focusing target line is sequentially changed to lines No.2 to No.16 by the receiving control section 18 and the steps from S14 to S26 are repeated with respect to in-phase sum signals of each line, and only in-phase signals not belonging to the boundary portion of in-phase sum signals Sj(k) of each line are added to the second focus index in series (S28).

For in-phase sum signals of lines No to No.16 subjected to the receive focusing using receive delay times based on the sound velocity setting No.2 in the manner described above, the boundary flag is not newly set and only in-phase sum signals not belonging to the boundary portion are added up to calculate the second focus index.

Thereafter, the sound velocity setting is sequentially changed to sound velocity setting No.3 to No.251 by the receiving control section 18, in-phase sum signals of the line No.1 to No.16 subjected to receive focusing using receive delay times calculated based on the sound velocity settings No to No.251 are calculated in series, and with respect to in-phase sum signals of the lines No.1 to No.16 corresponding to each of the sound velocity settings No.3 to No.251, only those not belonging to the boundary portion are added up to calculate third to $251^{th}$ focus indices.

With respect to in-phase sum signals of the lines No.1 to No.16 corresponding to each of the sound velocity settings No.1 to No.251, first to $251^{th}$ focus indices are eventually calculated, as illustrated in FIG. 3.

Then, a maximum focus index is selected from the first to $251^{th}$ focus indices obtained in the manner described above, and the sound velocity setting corresponding to the maximum focus index is obtained as the ambient sound velocity of the subject (S32).

So far, the ambient sound velocity obtaining method of the first embodiment has been described. In the ambient sound velocity obtaining method of the first embodiment, the added-up value of in-phase sum signals is used as the focus index, but other focus indices based on image intensity, such as a squared added-up value, may be used. Further, an arrangement may be adopted in which only in-phase sum signals not belonging to the boundary portion of those of lines No.1 to No.16 obtained with respect to each sound velocity setting are stored, then a spatial frequency spectrum is calculated from the stored in-phase sum signals, and the half width thereof may be used as the focus index. Further, the focus index is not limited to the half width of the spatial frequency spectrum and other focus indices based on the spatial frequency may be used. Still further, a focus index based on both of the image intensity, such as contrast or the like, and spatial frequency may be used.

According to the first embodiment described above, a true ambient sound velocity may be obtained using only the focus indices of the portion other than the boundary portion. In the case where an ultrasonic image is generated in the configuration in which the transmit focus is fixed and only the receive focus can be adjusted, it is preferable that ambient sound velocities are obtained for the boundary portion and the area other than the boundary portion, and receive focusing is performed on the boundary portion and portion other than the boundary portion using delay times based on the ambient sound velocities of the boundary portion and of the area other than the boundary portion respectively, instead of using only the ambient sound velocity obtained in the first embodiment.

Next, an ambient sound velocity obtaining method of a second embodiment will be described with reference to the flowchart of FIGS. 5A, 5B. In the ambient sound velocity obtaining method of the first embodiment, only the focus indices based on in-phase sum signals not belonging to the boundary portion are used, while in the ambient sound velocity obtaining method of the second embodiment, focus indices based on in-phase sum signals belonging to the boundary portion are also used and an ambient sound velocity is obtained in the case where the transmit focus is set to the boundary portion.

More specifically, during capturing of an ultrasonic image like that described above, the transmit focus of the ultrasonic waves transmitted from the ultrasonic probe 10 is set to a predetermined position No.1 and drive pulse voltage signals based on transmit delay times according to the position No.1 are outputted from the transmission control section 14 and an ultrasonic wave is transmitted from each ultrasonic transducer of the ultrasonic probe 10 (S40). Note that the transmit delay times here are values calculated in advance based on an assumed sound velocity setting set by assuming an ambient sound velocity in the subject.

In the present embodiment, as transmit focus No.i, No.1 to No.8 are preset in the scanning control section 16. More specifically, they are set at the following depths: No.1=12 mm, No.2=16 mm, No.3=20 mm, No.4=24 mm, No.5=28 mm, No.6=32 mm, No.7=36 mm, and No.8=40 mm.

Here, focus indices of boundary portion and portion other than the boundary portion, to be described later, are initialized (S42), but as nothing is stored as the focus indices when the transmit focus is No.1, it is assumed that the initialization is not performed here.

Then an echo due to reflection of the ultrasonic wave transmitted from each ultrasonic transducer is detected by each ultrasonic transducer, and the receive signal is outputted to the receive signal processing section 12 where the signal is subjected to amplification and A/D conversion before being outputted to the receiving control section 18.

The receiving control section 18 performs receive focusing on the receive signals using receive delay times calculated based on a predetermined sound velocity setting No.1 and calculates in-phase sum signals for a line No.1 and outputs the signals to the ambient sound velocity obtaining section 26 (S44, S46).

As sound velocity setting No.j, No.1 to No.251 of 1400 m/s to 1650 m/s are preset in the scanning control section 16 as in the first embodiment.

The line No.k represents in-phase sum signals of one column extending in a depth direction of the subject and is a line set within the range for obtaining the ambient sound velocity. In the present embodiment, 16 columns of lines No.1 to No.16 are used, as illustrated in FIG. 3.

Then, if the sound velocity setting used for the receive focusing is No.1, that is the sound velocity setting set first (S48), a determination is made as to whether or not each in-phase sum signal $S1(l)$ is that belonging to a boundary portion of the subject and a flag is set to the coordinate value of each in-phase sum signal of the line No.1, as in the first embodiment (S50). Note that l represents a depth of the subject within the range for obtaining the ambient sound velocity of the subject.

Then, an in-phase sum signal at a depth l to which the boundary flag=1 is set in step S50 is added up as a focus index for obtaining the ambient sound velocity of the boundary portion of the subject (S52, S54). On the other hand, an in-phase sum signal at a depth l to which the boundary flag=1 is not set in step S50 is added up as a focus index for obtaining the ambient sound velocity of the portion other than the boundary portion (S52, S56).

Each of all the in-phase sum signals $S1(l)$ of the line No.1 is determined whether it belongs to the boundary portion or the portion other than the boundary portion of the subject in the manner described above, and each in-phase signal belonging to the boundary portion is added to the focus index corresponding to the boundary portion and each in-phase signal not belonging to the boundary portion is added to the focus index corresponding to the portion other than the boundary portion (S58).

Thereafter, the receive focusing target line is sequentially changed to lines No.2 to No.16 by the receiving control section 18 and the steps from S46 to S56 are repeated with respect to in-phase sum signals of each line, and each in-phase signal belonging to the boundary portion is added to the focus index corresponding to the boundary portion and each in-phase signal not belonging to the boundary portion is added to the focus index corresponding to the portion other than the boundary portion (S60, S46 to S56).

With respect to each of the in-phase sum signals of lines No.1 to No.16 subjected to the receive focusing using receive delay times based on the sound velocity setting No.1, a determination is made as to whether or not it belongs to the boundary portion and the flag is set in the manner described above. Then, in-phase sum signals belonging to the boundary portion are added up to calculate a first focus index corresponding to the boundary portion while in-phase sum signals not belonging to the boundary portion are added up to calculate a first focus index corresponding to the portion other than the boundary portion.

Next, the receiving control section 18 changes the receive delay times to those calculated based on the sound velocity setting No.2 (S62, S44), calculates in-phase sum signals of line No.1 by performing receive focusing on receive signals using the changed receive delay times, and outputs the calculated in-phase sum signals to the ambient sound velocity obtaining section 26 (S46).

Next, if the sound velocity setting is No.2, that is, not the one set first (S46), the boundary flags are not newly set.

Then, using the same boundary flag as that set to coordinate value of the line No.1 when the sound velocity setting was No.1, a determination is made as to whether or not each in-phase sum signal belongs to the boundary portion (S52). That is, the value of the boundary flag set to the coordinate value of each line No.j when sound velocity setting is No.1 is the same as that set to the coordinate value of each line No.j when the sound velocity setting is No.2.

Then, in the step S52, an in-phase sum signal determined to belong to the boundary portion is added up as the focus index for obtaining the ambient sound velocity of the boundary of the subject while an in-phase signal determined not to belong to the boundary portion is added up as the focus index for obtaining the ambient sound velocity of the portion other than the boundary portion of the subject (S56).

Each of all the in-phase sum signals $S1(l)$ of the line No.1 is determined whether it belongs to a boundary portion or the portion other than the boundary portion of the subject in the manner described above, and each in-phase signal belonging to the boundary portion is added up to the focus index corresponding to the boundary portion while each in-phase signal belonging to the portion other than the boundary portion is added up to the focus index corresponding to the portion other than the boundary portion (S54, S56)

Thereafter, the receive focusing target line is sequentially changed to lines No.2 to No.16 by the receiving control section 18 and the steps from S46 to S56 are repeated with respect to in-phase sum signals of each line, and each in-phase signal belonging to the boundary portion is added up to the focus index corresponding to the boundary portion while each in-phase signal belonging to the portion other than the boundary portion is added up to the focus index corresponding to the portion other than the boundary portion (S54, S56).

For in-phase sum signals of lines No.2 to No.16 subjected to the receive focusing using receive delay times based on the sound velocity setting No.2 in the manner described above, the boundary flag is not newly set and only the calculation of the second focus index corresponding to the boundary portion in which only the in-phase sum signals belonging to the boundary portion are added up and the second focus index corresponding to the portion other than the boundary portion in which only the in-phase sum signals not belonging to the boundary portion are added up is performed.

Thereafter, the sound velocity setting is sequentially changed to sound velocity setting No.3 to No.251 by the receiving control section 18, in-phase sum signals of the line No.1 to No.16 subjected to receive focusing using receive delay times calculated based on the sound velocity settings No to No.251 are calculated in series, and with respect to in-phase sum signals of the lines No.1 to No.16 corresponding to each of the sound velocity settings No.3 to No.251, third to $251^{th}$ focus indices corresponding to the boundary portion are calculated by adding up only the in-phase sum signals belonging to the boundary portion and third to $251^{th}$ focus indices corresponding to the portion other than the boundary portion are calculated by adding up only the in-phase sum signals not belonging to the boundary portion (S62, S44 to S56).

That is, with respect to in-phase sum signals of the lines No.1 to No.16 corresponding to each of the sound velocity settings No.1 to No.251, first to $251^{th}$ focus indices corresponding to the boundary portion and those corresponding to the portion other than the boundary portion are eventually calculated.

Then, a maximum focus index is selected from the first to $251^{th}$ focus indices corresponding to the boundary portion obtained in the manner described above and the sound velocity setting corresponding to the maximum focus index is obtained as a provisional ambient sound velocity of the boundary portion and a maximum focus index is selected from the first to $251^{th}$ focus indices corresponding to the portion other than the boundary portion and the sound velocity setting corresponding to the maximum focus index is obtained as a provisional ambient sound velocity of the portion other than the boundary portion. Then, a difference between the provisional ambient sound velocities is calculated and stored (S64). The difference stored at this time is referred to as the difference of provisional sound velocity with respect to the transmit focus No.1.

Then, the transmit focus of the ultrasonic waves transmitted from the probe 10 is changed from the position No.1 to position No.2 (S66, S40). Drive pulse voltage signals based on the transmit delay times corresponding to the position No.2 are outputted from the transmission control section 14 and an ultrasonic wave is transmitted from each ultrasonic transducer of the ultrasonic probe 10.

Then, the first to $251^{th}$ focus indices corresponding to the boundary portion and the first to $251^{th}$ focus indices corresponding to the portion other than the boundary portion obtained when the transmit focus was No.1 are initialized (S42).

Then, with respect to the transmit focus No.2, the steps S44 to S62 are performed, whereby first to $251^{th}$ focus indices corresponding to the boundary portion and first to $251^{th}$ focus indices corresponding to the portion other than the boundary portion are calculated.

Then, a maximum focus index is selected from the first to $251^{th}$ focus indices corresponding to the boundary portion and the sound velocity setting corresponding to the maximum focus index is obtained as a provisional ambient sound velocity of the boundary portion and a maximum focus index is selected from the first to $251^{th}$ focus indices corresponding to the portion other than the boundary portion and the sound velocity setting corresponding to the maximum focus index is obtained as a provisional ambient sound velocity of the portion other than the boundary portion. Then, a difference between the provisional ambient sound velocities is stored as the difference of provisional ambient sound velocity with respect to the transmit focus No.2.

Thereafter, the transmit focus position is sequentially changed to No.3 to No.8 and each difference of provisional ambient sound velocity corresponding to each of the transmit focus No.3 to No.8 are calculated in series and stored (S66, S40 to S64).

The differences of provisional ambient sound velocities corresponding to the transmit focuses No.1 to No.8 stored in the manner described above are compared in magnitude, and the transmit focus position corresponding to a minimum difference of those differences is selected. Then, the provisional ambient sound velocity of the portion other than the boundary portion at the transmit focus position where the difference of provisional ambient sound velocity becomes minimal, that is, the transmit focus position where the provisional ambient sound velocity of the boundary portion becomes closest to that of the portion other than the boundary portion is obtained as the true ambient sound velocity of the subject (S68).

So far, the ambient sound velocity obtaining method of the second embodiment has been described.

Then, the ambient sound velocity of the subject obtained by the ambient sound velocity obtaining method of the first or second embodiment may be displayed on the monitor 24 as numerical information upon receipt of an operator instruction. Alternatively, an arrangement may be adopted in which transmit delay times based on the obtained ambient sound velocity and receive delay times are calculated, then transmit focusing is performed base on the calculated transmit delay times and receive focusing is performed using the receive delay times to generate an ultrasonic image signal, and an ultrasonic image based on the ultrasonic image signal is displayed on the monitor 24.

In the description of the second embodiment, the provisional ambient sound velocity of the portion other than the boundary portion at the transmit focus position where the difference of provisional ambient sound velocity becomes minimal, that is, the transmit focus position where the provisional ambient sound velocity of the boundary portion becomes closest to that of the portion other than the boundary portion is obtained as the true ambient sound velocity of the subject, but the provisional ambient sound velocity of the boundary portion at the transmit focus position where the provisional ambient sound velocity of the boundary portion becomes closest to that of the portion other than the boundary portion may be obtained as the true ambient sound velocity of the subject.

The invention claimed is:

1. An ambient sound velocity obtaining method comprising:
   transmitting an ultrasonic wave into a subject from an ultrasonic probe;
   reflecting a reflection wave from the subject by the transmission of the ultrasonic wave being received by the ultrasonic probe to obtain a receive signal;
   performing receive focusing on the receive signal using receive delay times based on a plurality of sound velocity settings to obtain in-phase sum signals with respect to each sound velocity setting; and
   obtaining an ambient sound velocity of the subject based on the obtained in-phase sum signals with respect to each sound velocity setting,
   wherein:
      the in-phase sum signals are automatically separated with respect to each sound velocity setting into an in-phase sum signal corresponding to a boundary portion in the subject at which mirror reflection occurs and an in-phase sum signal corresponding to a portion other than the boundary portion, based on the relationships of the sizes of in-phase sum signals which are arranged adjacent to each other in the depth direction of the subject;
      an index is obtained based on at least either one of the in-phase sum signal corresponding to the boundary portion and the in-phase sum signal corresponding to the portion other than the boundary portion; and
      the ambient sound velocity is obtained based on the obtained index.

2. The ambient sound velocity obtaining method of claim 1, wherein:
   the obtaining the index comprises obtaining an index based on the in-phase sum signal corresponding to the boundary portion and an index based on the in-phase sum signal corresponding to the portion other than the boundary portion; and
   the obtaining the ambient sound velocity comprises obtaining the ambient sound velocity based on the obtained index based on the in-phase sum signal corresponding to the boundary portion and the index based on the in-phase sum signal corresponding to the portion other than the boundary portion.

3. An ambient sound velocity obtaining method comprising:
  transmitting an ultrasonic wave into a subject from an ultrasonic probe;
  obtaining a reception signal by receiving a reflection wave reflected from the subject by the transmission of the ultrasonic wave;
  performing focusing on the reception signal using reception delay times based on a plurality of sound velocity settings;
  obtaining in-phase sum signals with respect to each sound velocity setting based on the performed focusing; and
  obtaining an ambient sound velocity of the subject based on the obtained in-phase sum signals with respect to each sound velocity setting,
  wherein:
    the ultrasonic wave focused on a plurality of transmit focus positions is transmitted with respect to each transmit focus position;
    the in-phase sum signals with respect to each sound velocity setting are obtained for each transmit focus position, and automatically separated into an in-phase sum signal corresponding to a boundary portion in the subject at which mirror reflection occurs and an in-phase sum signal corresponding to a portion other than the boundary portion, based on the relationships of the sizes of in-phase sum signals which are arranged adjacent to each other in the depth direction of the subject;
    an index based on the in-phase sum signal corresponding to the boundary portion and an index based on the in-phase sum signal corresponding to the portion other than the boundary portion are obtained for each of the transmit focus positions; and
  obtaining the ambient sound velocity comprises:
    obtaining a difference between a provisional ambient sound velocity obtained based on the index of the boundary portion and a provisional ambient sound velocity obtained based on the index of the portion other than the boundary portion with respect to each focus position; and
    obtaining a provisional ambient sound velocity obtained based on the index of the boundary portion or the index of the portion other than the boundary portion corresponding to a transmit focus position where the difference obtained becomes minimal as the ambient sound velocity of the subject.

4. The ambient sound velocity obtaining method of claim 1, wherein the boundary portion is determined based on a ratio between the in-phase sum signals disposed in the depth direction of the subject, or a first or second derivative value using the logarithm of the in-phase sum signals.

5. An ambient sound velocity obtaining apparatus, comprising:
  a transmission control section for transmitting an ultrasonic wave into a subject from an ultrasonic probe;
  a receiving control section for receiving a reflection wave reflected from the subject by the transmission of the ultrasonic wave by the ultrasonic probe to obtain a receive signal and performing receive focusing on the obtained receive signal using receive delay times based on a plurality of sound velocity settings to obtain in-phase sum signals with respect to each sound velocity setting; and
  an ambient sound velocity obtaining section for obtaining an ambient sound velocity of the subject based on the in-phase sum signals obtained by the receiving control section with respect to each sound velocity setting,
  wherein the ambient sound velocity obtaining section is a section that automatically separates the in-phase sum signals with respect to each sound velocity setting into an in-phase sum signal corresponding to a boundary portion in the subject at which mirror reflection occurs and an in-phase sum signal corresponding to a portion other than the boundary portion based on the relationship of the sizes of in-phase sum signals which are arranged adjacent to each other in the depth direction of the subject, obtains an index based on at least either one of the in-phase sum signal corresponding to the boundary portion and the in-phase sum signal corresponding to the portion other than the boundary portion, and obtains the ambient sound velocity based on the obtained index.

6. The ambient sound velocity obtaining apparatus of claim 5, wherein the ambient sound velocity obtaining section is a section that obtains an index based on the in-phase sum signal corresponding to the boundary portion and an index based on the in-phase sum signal corresponding to the portion other than the boundary portion and obtains an ambient sound velocity based on the obtained index based on the in-phase sum signal corresponding to the boundary portion and the index based on the in-phase sum signal corresponding to the portion other than the boundary portion.

7. An ambient sound velocity obtaining apparatus, comprising:
  a transmission control section for transmitting an ultrasonic wave into a subject from an ultrasonic probe:
  a receiving control section for receiving a reflection wave reflected from the subject by the transmission of the ultrasonic wave by the ultrasonic probe to obtain a receive signal and performing receive focusing on the obtained receive signal using receive delay times based on a plurality of sound velocity settings to obtain in-phase sum signals with respect to each sound velocity setting; and
  an ambient sound velocity obtaining section for obtaining an ambient sound velocity of the subject based on the in-phase signals obtained by the receiving control section with respect to each sound velocity setting,
  wherein:
    the transmission control section is a section that transmits the ultrasonic wave focused on a plurality of transmit focus positions with respect to each focal position, and
    the ambient sound velocity obtaining section is a section that obtains in-phase sum signals with respect to each of the velocity settings for each of the transmit focus positions, automatically separate the in-phase sum signals for each of the velocity settings into an in-phase sum signal corresponding to a boundary portion at which mirror reflection occurs and an in-phase sum signal corresponding to a portion other than the boundary portion, based on the relationships of the sizes of in-phase sum signals which are arranged adjacent to each other in the depth direction of the subject, obtains an index based on the in-phase sum signal corresponding to the boundary portion and an index based on the in-phase sum signal corresponding to the portion other than the boundary portion with respect to each transmit focus position, obtains a difference between a provisional ambient sound velocity obtained base on the index of the boundary portion and a provisional ambient sound velocity obtained based on the index of the portion other than the boundary portion with respect to each focus position, and obtains a provisional ambient sound velocity obtained based on the index of the boundary portion or the index of the portion other than the boundary portion corresponding to a transmit focus position where the difference obtained becomes minimal as the ambient sound velocity of the subject.

8. The ambient sound velocity obtaining apparatus of claim 5, wherein the ambient sound velocity obtaining section is a section that determines the boundary portion based on a ratio between the in-phase sum signals disposed in the depth direction of the subject, or a first or second derivative value using the logarithm of the in-phase sum signals.

9. The ambient sound velocity obtaining method of claim 1, wherein the boundary portion is the surface of a structure in the subject.

10. The ambient sound velocity obtaining method of claim 1, wherein the automatic separating is based on a logarithm for a ratio between the adjacent in-phase sum signals $S1(k)$ and $S1(k+1)$ and a determination is made as to whether or not the absolute value of the logarithm is greater than a predetermined threshold value, and wherein if the absolute value is greater than the predetermined threshold value, the in-phase sum signal is determined to belong to the boundary portion and wherein the index is obtained without using the in-phase sum signal corresponding to the boundary portion.

* * * * *

UNITED STATES PATENT AND TRADEMARK OFFICE
CERTIFICATE OF CORRECTION

| | | |
|---|---|---|
| PATENT NO. | : 9,291,601 B2 | Page 1 of 1 |
| APPLICATION NO. | : 13/638501 | |
| DATED | : March 22, 2016 | |
| INVENTOR(S) | : Kimito Katsuyama | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 485 days.

Signed and Sealed this
Fourteenth Day of June, 2016

Michelle K. Lee
*Director of the United States Patent and Trademark Office*